United States Patent
Adkins et al.

(10) Patent No.: US 6,823,720 B1
(45) Date of Patent: Nov. 30, 2004

(54) METHOD FOR CHEMICAL SENSING USING A MICROFABRICATED TEETER-TOTTER RESONATOR

(75) Inventors: Douglas Ray Adkins, Albuquerque, NM (US); Edwin J. Heller, Albuquerque, NM (US); Randy J. Shul, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 110 days.

(21) Appl. No.: 10/436,596

(22) Filed: May 12, 2003

(51) Int. Cl.[7] .............................................. G01N 11/10
(52) U.S. Cl. ...................... 73/54.25; 73/24.06; 73/579
(58) Field of Search ........................... 73/54.25, 54.41, 73/64.53, 61.79, 24.01, 24.06, 579

(56) References Cited

U.S. PATENT DOCUMENTS

| | | | |
|---|---|---|---|
| 4,248,092 A | * 2/1981 | Vasile et al. | 73/643 |
| 4,567,451 A | * 1/1986 | Greenwood | 331/155 |
| 5,813,280 A | * 9/1998 | Johnson et al. | 73/643 |
| 5,836,203 A | 11/1998 | Martin et al. | 73/579 |
| 6,272,907 B1 | * 8/2001 | Neukermans et al. | 73/105 |
| 6,387,329 B1 | * 5/2002 | Lewis et al. | 422/98 |
| 6,397,661 B1 | * 6/2002 | Grimes et al. | 73/24.06 |

OTHER PUBLICATIONS

Grate, J.W., "Acoustic Wave Microsensor Arrays for Vapor Sensing," *Chem. Rev. 2000*, 100, 2627–2648.
Martin, et al., "Gas Sensing with Acoustic Devices," *Proc. IEEE Ultrasonics Symposium*, 423 (1996).
Martin et al., "Flexural plate wave resonator excited with Lorentz forces," *J. Appl. Phys.* 83(9), 4589 (1998).
Givens, et al., "A high sensitivity wide dynamic range magnetometer designed on a xylophone resonator," *Appl. Phys. Lett* 69(18), 2755 (1996).

* cited by examiner

*Primary Examiner*—Hezron Williams
*Assistant Examiner*—Jacques M. Saint-Surin
(74) *Attorney, Agent, or Firm*—Kevin W. Bieg

(57) ABSTRACT

A method for sensing a chemical analyte in a fluid stream comprises providing a microfabricated teeter-totter resonator that relies upon a Lorentz force to cause oscillation in a paddle, applying a static magnetic field substantially aligned in-plane with the paddle, energizing a current conductor line on a surface of the paddle with an alternating electrical current to generate the Lorentz force, exposing the resonator to the analyte, and detecting the response of the oscillatory motion of the paddle to the chemical analyte. Preferably, a chemically sensitive coating is disposed on at least one surface of the paddle to enhance the sorption of the analyte by the paddle. The concentration of the analyte in a fluid stream can be determined by measuring the change in the resonant frequency or phase of the teeter-totter resonator as the chemical analyte is added to or removed from the paddle.

20 Claims, 9 Drawing Sheets

METHOD FOR CHEMICAL SENSING USING A MICROFABRICATED TEETER-TOTTER RESONATOR

STATEMENT OF GOVERNMENT INTEREST

This invention was made with Government support under contract no. DE-AC04-94AL85000 awarded by the U. S. Department of Energy to Sandia Corporation. The Government has certain rights in the invention.

CROSS-REFERENCE TO RELATED APPLICATIONS

This application is related to SD-7221, "Microfabricated Teeter-Totter Resonator," filed of even date with this application.

FIELD OF THE INVENTION

The present invention relates to chemical sensing and, more particularly, to a method for chemical sensing using a microfabricated teeter-totter resonator.

BACKGROUND OF THE INVENTION

Microfabricated chemical sensors based on acoustic devices combine a chemically sensitive interface, which sorbs chemical species (i.e., analytes) from the environment, with a physical transducer that provides an electrical output proportional to the amount of sorbed species. Two commonly used acoustic devices for chemical sensing include surface acoustic wave (SAW) and resonant microsensors, such as the flexural plate wave (FPW) resonator. See S. J. Martin et al., "Gas Sensing with Acoustic Devices," *Proc. IEEE Ultrasonics Symposium*, 423 (1996), which is incorporated herein by reference.

SAW sensors rely on the electrical excitation of a surface acoustic wave in a piezoelectric substrate. Typically, a wave is established on a quartz surface and the collection of analyte mass on the surface is reflected in the propagation of the surface wave. The high quality factor, Q, and low insertion loss of SAW chemical sensors makes them extremely stable in an oscillator circuit, resulting in low detection limits. SAW sensors can detect sub nanogram-levels of chemical analytes. However, SAW sensors typically operate at hundreds of megahertz frequencies, complicating the design and integration of oscillator circuitry.

A resonator comprises a vibrating element of a certain shape. Depending on the shape, the resonator can support several types of vibrations, e.g., longitudinal, transverse, torsional, and lateral, that can have a number of vibrational modes or resonances. The stress, mass, or shape of the resonator is typically designed such that one of these modes dominates and the resonant frequency of the dominant mode is matched to a driving excitation signal. When used as a chemical sensor, the collection of analyte mass or fluid loading on the surface of the resonator is reflected as a change in the resonant frequency or the amplitude of the vibration.

Resonators that operate on magnetic actuation principles are particularly attractive for chemical sensing applications, due to their large dynamic range and high sensitivity. Electromagnetic sensors rely on a Lorentz force, generated by an alternating electrical current flowing in the resonator interacting with an external magnetic field, to excite a mechanical vibration in the structure.

A magnetically excited FPW (mag-FPW) resonator is described in S. J. Martin et al., "Flexural plate wave resonator excited with Lorentz forces," *J. Appl. Phys.* 83(9), 4589 (1998) and U.S. Pat. No. 5,836,203, which are incorporated herein by reference. The mag-FPW resonator comprises current lines patterned on a silicon nitride membrane that is suspended on a silicon frame. A Lorentz force is created by the interaction of an alternating surface current flowing in the current lines and an in-plane static magnetic field perpendicular to the current flow direction. Preferential coupling to a particular membrane mode is achieved by positioning the current lines along antinodes of the longitudinal mode. When the alternating current has the natural frequency of the mag-FPW resonator, a large amplitude standing wave is set up in the membrane wave plate. The motion of the current conductor lines in the magnetic field in turn induces a back electromotive force (back-emf) opposing the motion. This back-emf can be detected as an increase in impedance of the current lines.

Because the confinement of kinetic energy is in a thin, low-mass membrane, the FPW sensor can have a very high mass sensitivity. Also, because the wave velocity in the FPW membrane is much less than in a solid substrate, the operating frequency of a FPW device is much lower than in a SAW device, resulting in simpler oscillator electronics. In addition, FPW resonators can be made with micromachining processes in a silicon wafer and can be integrated with microelectronic circuits. However, the temperature-dependent tension variation in the membrane, due to the differential thermal expansion of the silicon nitride membrane relative to the silicon frame, make the FPW operation very sensitive to temperature drift.

Therefore, a need remains for a method for chemical sensing that uses a microfabricated resonator having a high Q-factor, low operating frequency, high mass sensitivity, and low temperature drift. The method of the present invention uses a microfabricated teeter-totter resonator that provides a Q-factor, operating frequency, and mass sensitivity comparable to the FPW resonators, but with much better temperature stability. In particular, the teeter-totter resonator is about three orders of magnitude less sensitive to temperature drift than the FPW resonator.

SUMMARY OF THE INVENTION

The present invention is directed to a method for sensing a chemical analyte in a fluid stream, the method comprising providing a microfabricated teeter-totter resonator, the resonator comprising a frame, a paddle having a first end and a second end and wherein the paddle is pivotably anchored to the frame by pivot arms at each end of the paddle, the pivot arms defining an axis of rotation of the paddle, a current conductor line on a surface of the paddle that is displaced from the axis of rotation of the paddle, means for applying a static magnetic field aligned substantially in-plane with the paddle and substantially perpendicular to the current conductor line and the axis of rotation, and means for energizing the current conductor line with an alternating electrical current; applying the static magnetic field; energizing the current conductor line with the alternating electrical current to excite an oscillatory motion of the paddle about the axis of rotation; exposing the resonator to the chemical analyte; and detecting the response of the oscillatory motion of the paddle to the chemical analyte. Preferably, a chemically sensitive coating is disposed on at least one surface of the paddle to enhance the sorption of the analyte from the fluid stream. The detecting can comprise measuring the change in resonant frequency or phase or rotational displacement of the oscillatory motion of the paddle due to fluid loading or sorption of the analyte by the paddle.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
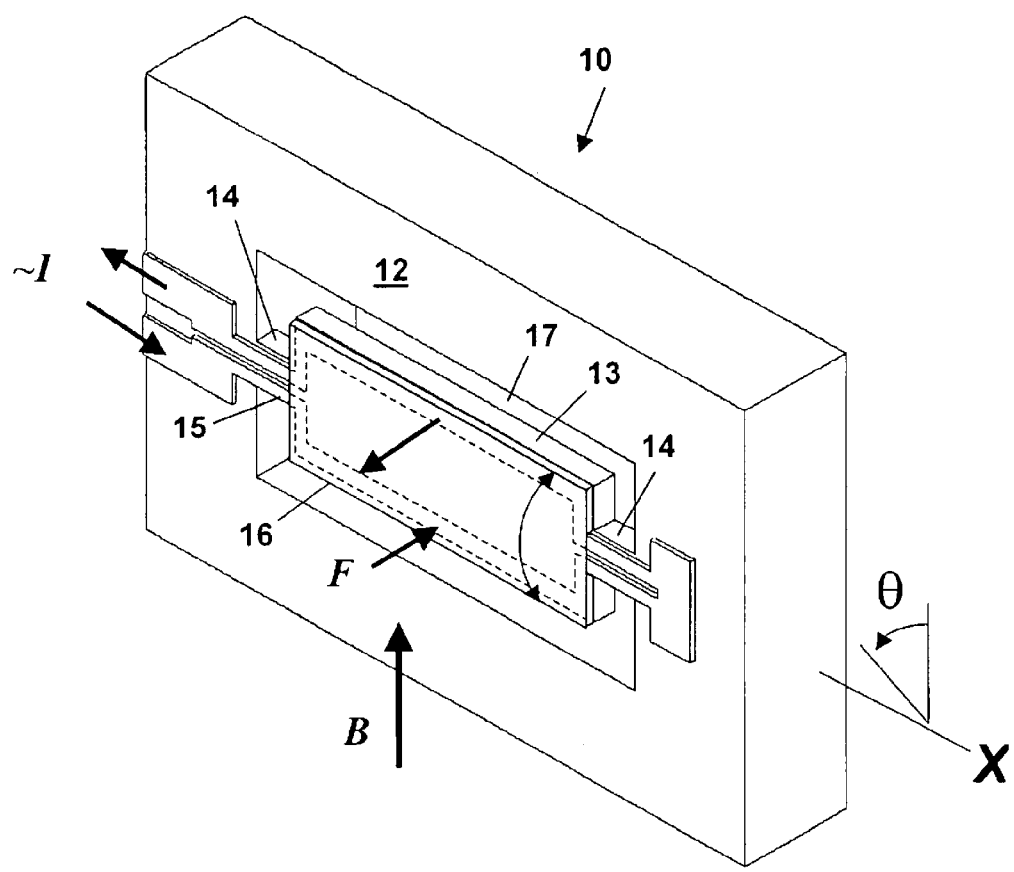
FIG. 1 shows a schematic illustration of a microfabricated teeter-totter resonator.

The present invention provides a method for chemical sensing using a microfabricated teeter-totter resonator that relies on the Lorentz force to excite a torsional oscillation in a paddle that is sensitive to fluid loading or the sorption of a chemical analyte in a fluid stream. In FIG. 1 is shown a schematic illustration of the microfabricated teeter-totter resonator 10, comprising a frame 12, a paddle 13, pivot arms 14, a current conductor line 15, means for applying a static magnetic field B in the plane of the paddle 13, and means for energizing the current conductor line 15 with an alternating current I. The frame 12 is preferably a non-magnetic structural material, which typically can be silicon. Alternatively, other structural materials can be used. The paddle 13 is preferably a non-magnetic, semiconducting or insulating thin plate, which typically can be silicon, polysilicon, silicon nitride, silicon dioxide, or a polymer. Alternatively, other thin-film materials can be used. Alternatively, the paddle 13 can be a conducting material with a thin insulating film (not shown) on the surface to provide electrical isolation of the current conductor line 15. The paddle 13 is preferably rectangular in shape, although other shapes can also be used. For use as a chemical sensor, the paddle 13 preferably further comprises a chemically sensitive coating. 16 disposed on one or both surfaces of the paddle 13 for sorption of the chemical analyte. Alternatively, the paddle material itself can sorb or collect the analyte without the need for the coating 16. Alternatively, fluid loading can alter oscillatory motion of the paddle 13. The pivot arms 14 pivotably anchor the oscillating paddle 13 to the stationary frame 12. The pivot arms 14 therefore define an axis of rotation X in the plane of the paddle 13. The rotational axis X is preferably the longitudinal axis of a rectangular paddle. A clearance gap 17 is provided to allow free oscillation of the paddle 13 within a cavity of the stationary frame 12 about the rotational axis X. The current conductor line 15 is displaced from the rotational axis X of the paddle 13. Preferably, the conductor line 15 runs around the periphery of the paddle 13 to provide a large Lorentz force F.

The source of the magnetic field B can be a conventional permanent magnet, direct-current (DC) coils, or the like. The magnetic field B is aligned substantially parallel to the plane of the paddle 13 and substantially perpendicular to the current direction in the conductor line 15 and the axis of rotation X. As shown in FIG. 1, application of an electrical current I to the conductor line 15 generates a surface-normal Lorentz force F directed according to the right-hand rule. The torque resulting from the Lorentz force F is resisted by the torsional spring restoring force resulting from the twisting of the pivot arms 14. Furthermore, because of the static B field, an alternating electrical current I through the conductor line 15 generates a reversing direction of the Lorentz force F on the paddle 13, causing the paddle 13 to oscillate from its rest position about the axis of rotation X.

At a certain frequency, a resonant mode is established and the paddle 13 undergoes maximum oscillations. The resonant frequency can be determined from the differential equation-of-motion for a teeter-totter resonator:

$$J\ddot{\theta} + C_t\dot{\theta} + k\theta = T \quad (1)$$

where $\theta$ is the torsional angle of the paddle oscillation about the axis of rotation X, J is the polar moment of inertia of the paddle cross-section about the rotational axis X, $C_t$ is the damping coefficient due to structural damping and viscous dissipation due to fluid loading, and T is the time-dependent applied torque.

Figure 2:
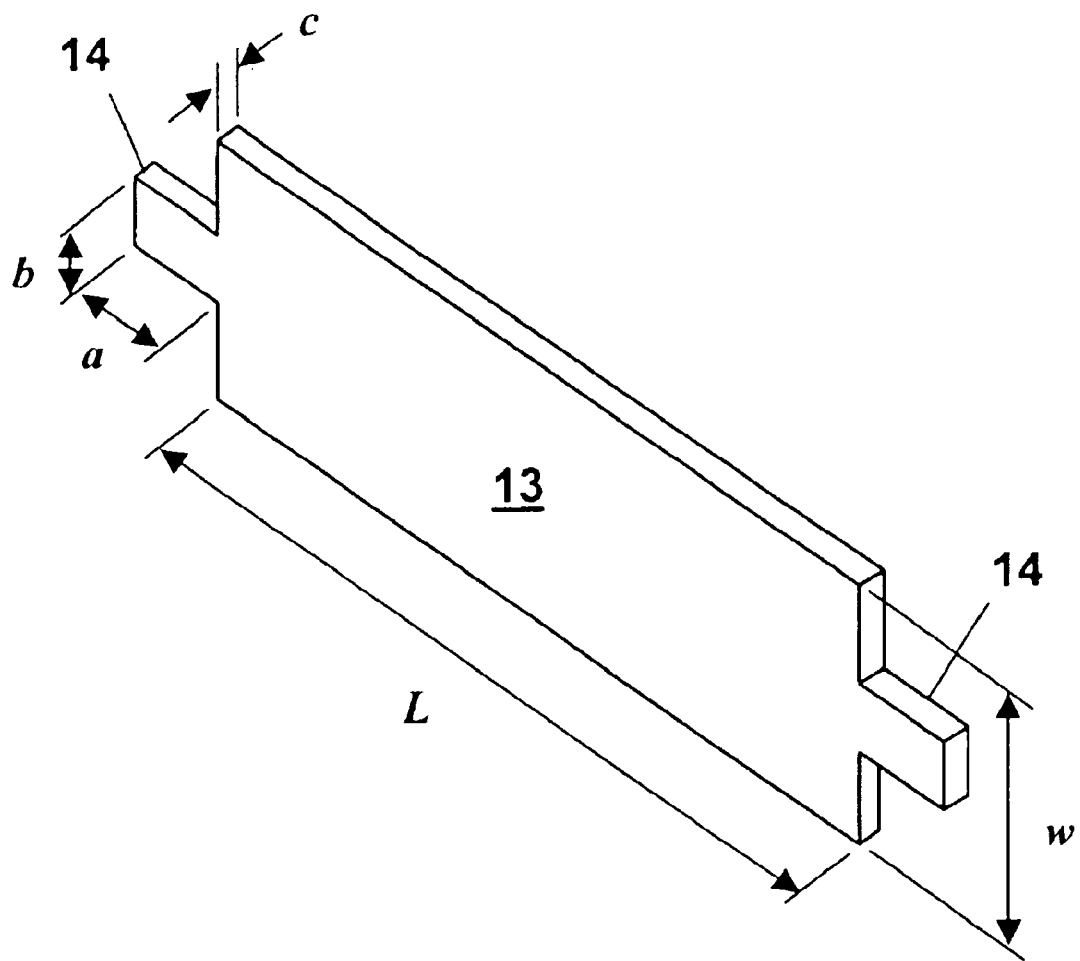
FIG. 2 shows a schematic illustration of a rectangular paddle of a microfabricated teeter-totter resonator.

Shown in FIG. 2 is a schematic illustration of a rectangular paddle 13 (i.e., neglecting the coating 16). The rectangular paddle 13 has a width w, length L, thickness c, and effective density $\rho$. The pivot arms 14 have a length a and width b. Therefore, the polar moment of inertia of the rectangular cross-section is $J = \rho w c L(c^2+w^2)/12$. For a current conductor line 15 running around the perimeter of the rectangular paddle 13, the applied torque is T=Fw=BILw, where B is the static magnetic flux, and I is the time-varying current through the conductor line 15. The torsional spring constant of the pivot arms 14 is $$k = 2\beta b c^3 G/a \quad (2)$$

where G is the shear modulus of elasticity of the pivot arm material. $\beta$ is a parameter that depends on the ratio b/c of the long side to the short side of the rectangular cross-section of the pivot arm 14 that is twisted. For a thin section (b>>c), $\beta$ is approximately ⅓.

The steady-state solution to the equation-of-motion, eq. (1), has the form $$\theta = \Theta \exp(j\omega t) = |\Theta|\exp j(\omega t - \phi_d) \quad (3)$$

where the amplitude is $$|\Theta| = \frac{BwLI/k}{\sqrt{(1-r^2)^2 + (2\zeta r)^2}} \quad (4)$$

where $r=\omega/\omega_n$, and $\zeta = C_t/2\sqrt{kJ} = 1/2Q$. Q is the mechanical quality factor of the resonator. The phase of the rotational displacement relative to the drive current is $$\phi_d = \tan^{-1}\frac{2\zeta r}{1-r^2} \qquad (5)$$

The natural resonant frequency of oscillation is $$\omega_n = \sqrt{k/J} \qquad (6)$$

Therefore, changing the cross section or length of the pivot arms 14 or the dimensions or mass of the paddle 13 will alter the resonant frequency $\omega_n$ and the phase $\phi_d$ of the oscillations at resonance. In particular, for chemical sensing applications, both the resonant frequency $\omega_n$ and phase $\phi_d$ are changed, through the dependence of the moment of inertia J on the absorbed mass, when a chemical analyte is absorbed or desorbed from the chemically selective coating 16 or the paddle 13. The resonant frequency $\omega_n$ and phase $\phi_d$ can also be altered by changes in the damping coefficient $C_t$ due to fluid loading. Importantly, the teeter-totter resonator 10 is relatively insensitive to temperature drift, since the shear modulus of elasticity G, which determines the torsional spring constant k, has only a small variation with temperature.

The motion of the current conductor line 15 in the magnetic field B induces a back-emf in the conductor line 15 opposing the motion. The back-emf is $$E = BwL\frac{d\theta}{dt} \qquad (7)$$

and it is electrically manifested as a change in the impedance (i.e., "motional resistance") of the current conductor line 15. The amplitude of the resonator impedance is $$Z = \frac{V}{I} = Z_0 + Z_D = Z_0 - \frac{BwLj\omega\Theta}{I} = |Z|\exp(j\phi_z) \qquad (8)$$

where $Z_0$ is the DC resistance of the resonator, $Z_D$ is the impedance change due to the back-emf, and $$|Z| = \frac{(BwL)^2}{J\omega_n} \sqrt{\left(\frac{Z_0 J\omega_n}{(BwL)^2 r} + \frac{2r\zeta}{(1-r^2)^2+(2r\zeta)^2}\right)^2 + \left(\frac{(1-r^2)}{(1-r^2)^2+(2r\zeta)^2}\right)^2} \qquad (9)$$

$$\phi_z = \arctan\left(\frac{(1-r^2)}{\frac{Z_0 J\omega_n}{(BwL)^2 r}[(1-r^2)^2+(2r\zeta)^2]+2r\zeta}\right) \qquad (10)$$

The impedance change $Z_D$ can be used to detect the teeter-totter resonances. In a one-port device, the excitation and detection of the oscillation of the teeter-totter resonator 10 and its resonant frequency $\omega_n$ can be obtained directly through the ratio of the drive voltage to the drive current (i.e., an impedance response). Alternatively, in a two-port device, a second conductor line can be run in a different region of the paddle 13 (e.g., on the back side of the paddle 13) and the oscillation excited by the conductor line 15 can be detected as an output voltage induced in the second conductor line.

Figure 3:
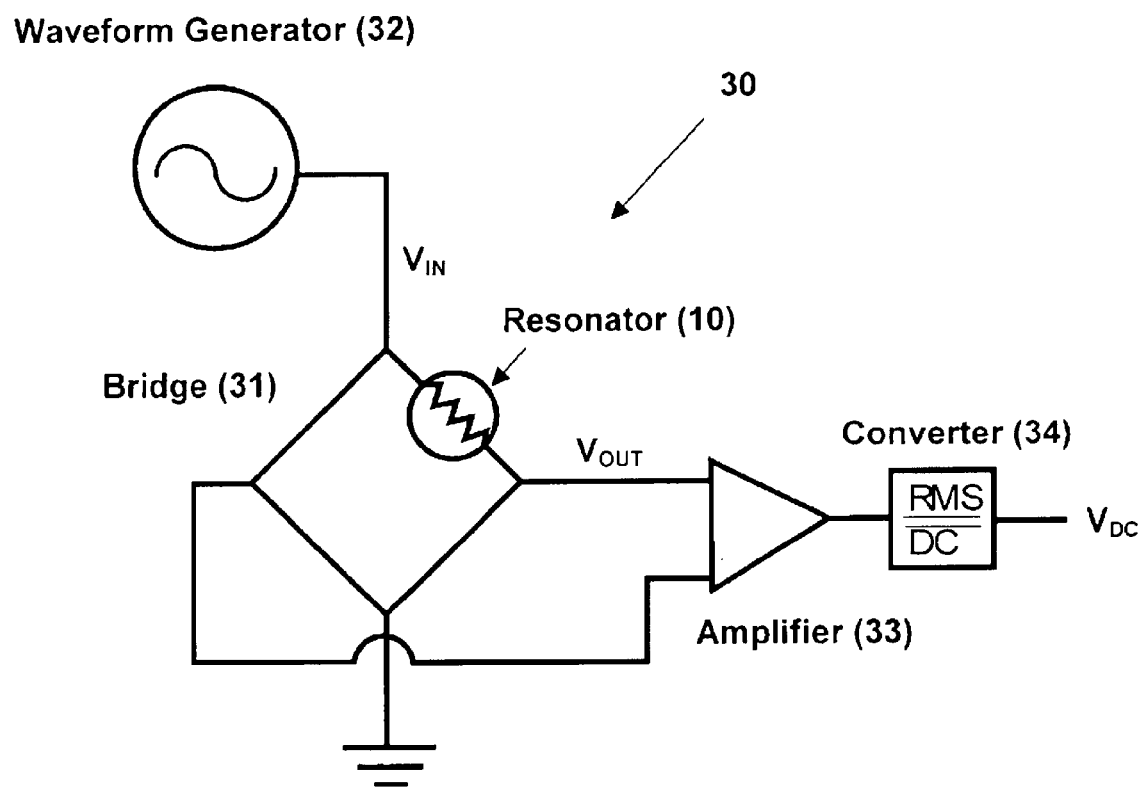
FIG. 3 shows a simple excitation and detection circuit with the microfabricated teeter-totter resonator forming the active leg of a Wheatstone bridge.

The impedance response of the teeter-totter resonator 10 can be measured with an electronic oscillator circuit and a bridge circuit. In FIG. 3 is shown a simple excitation and detection circuit 30 that can be used to excite the resonator 10 and detect the impedance change $Z_D$ due to the back-emf.

The simple circuit 30 comprises a Wheatstone bridge circuit 31, a waveform generator 32 to drive the bridge 31 with a sinusoidal supply voltage $V_{IN}$, an operational amplifier 33 to amplify the bridge voltage $V_{OUT}$, and an RMS-to-DC converter 34 to convert the amplifier output to a DC output voltage $V_{DC}$. A single teeter-otter resonator 10 forms the active leg of the bridge circuit 31. Therefore, the bridge output voltage is proportional to the relative change of the resonator's impedance according to $$V_{OUT} = \left(\frac{1}{2} - \frac{Z_0}{2Z_0 + Z_D}\right)V_{IN} \qquad (11)$$

where $Z_0$ is the ohmic resistance of the current conductor line 15 and $Z_D$ is the impedance change resulting from the back-emf. When the resonator 10 is not operating at resonance, the bridge 31 is balanced and the differential output $V_{OUT}$ from the bridge 31 is zero. At resonance, the resonator's impedance increases, due to the back-emf, and the bridge 31 is unbalanced, resulting in an AC bridge voltage $V_{OUT}$ at the input of the amplifier 33. This AC bridge voltage $V_{OUT}$ can be amplified and converted to a DC output voltage $V_{DC}$ by the RMS-to-DC converter 34.

Figure 4:
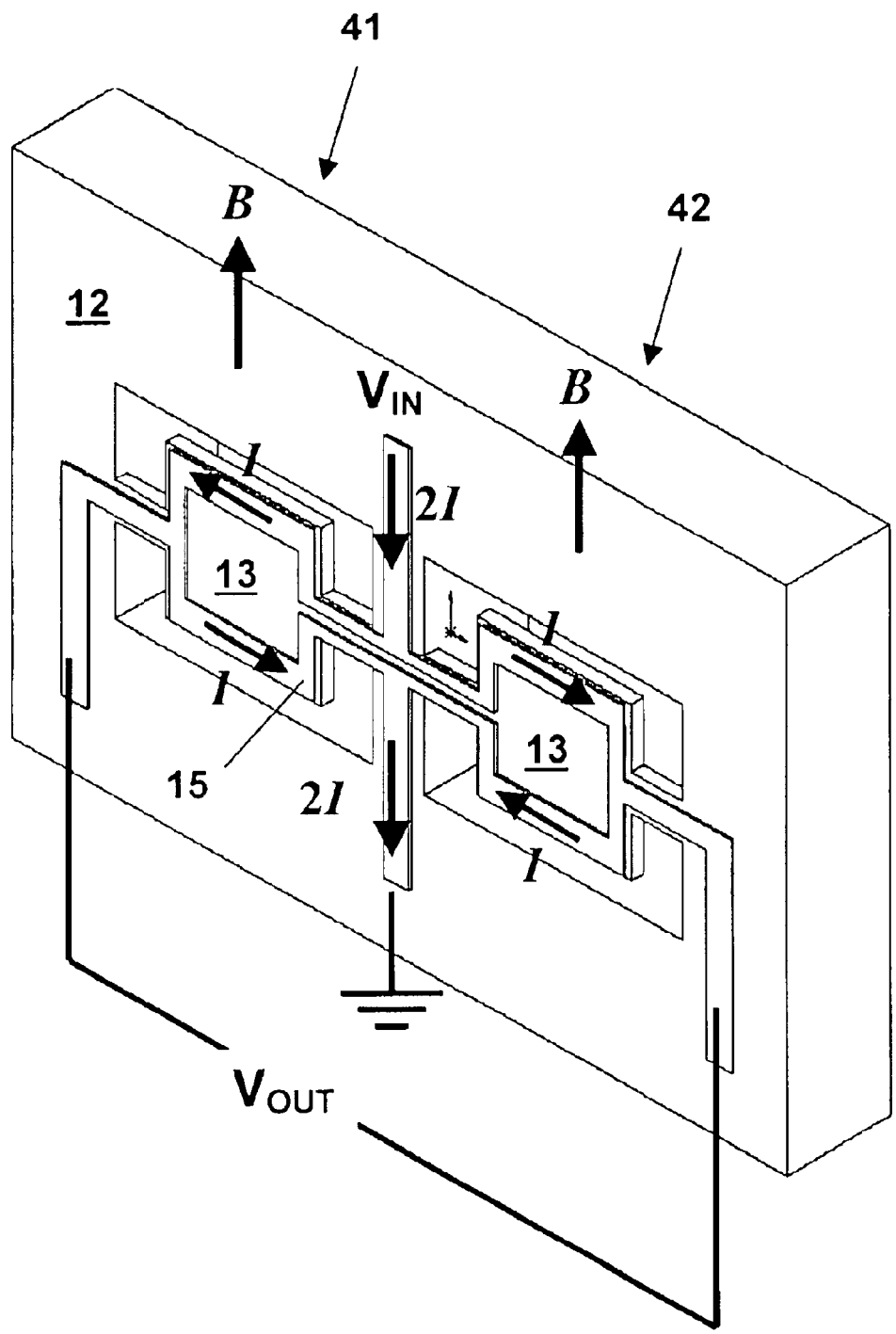
FIG. 4 shows two counter-rotating teeter-totter resonators that provide a Wheatstone bridge with four active legs.

The sensitivity and the linearity of detection can be improved by using two counter-rotating teeter-totter resonators opposed to each other in a bridge configuration with four active legs. In FIG. 4 is shown two counter-rotating teeter-totters 41 and 42 on a common substrate 12 with a common current conductor line 15 that runs around the periphery of the two paddles 13. For chemical sensing, one or more of the surfaces of each of the paddles 13 can be coated with a chemically sensitive material.

Identical resonators 41 and 42 can be configured as opposing legs in a Wheatstone bridge circuit. The bridge voltage $V_{OUT}$ is given then by $$V_{OUT} = Z_D I = \frac{Z_D}{Z_0} V_{IN} \qquad (12)$$

By measuring $V_{OUT}$, the resonant frequency of the counter-rotating teeter-totter resonators can be determined. If $V_{IN}$ is not at the resonant frequency $\omega_n$ of the counter-rotating resonators 41 and 42, the oscillations and therefore the impedance change $Z_D$ due to the back-emf are small and the bridge is balanced, so that $V_{OUT}$ will be zero. $V_{OUT}$ reaches a maximum when the oscillations and back-emf are largest at the resonant frequency $\omega_n$. Therefore, this counter-rotating resonator bridge configuration can be used to more sensitively detect changes in the resonant frequency $\omega_n$ due to mass accumulation or fluid loading on the paddles 13.

The teeter-totter resonator 10 can be fabricated by micromachining techniques generally known to the integrated circuits manufacturing industry. Such methods enable batch fabrication and monolithic integration of the resonator with on-chip electronic circuitry.

In FIGS. 5a–5i are shown cross-sectional views of a method to fabricate the teeter-totter resonator 10, starting with a silicon-on-insulator (SOI) substrate having a top silicon layer separated from a silicon substrate by an intermediate buried $SiO_2$ layer. The SOI method comprises the steps of depositing the current conductor line 15 on the top silicon layer; patterning the top silicon layer to define the paddle 13, the pivot arms 14, and the inner wall of the frame 12; forming a cavity in the backside of the silicon substrate, underneath the paddle, pivot arms, and clearance gap regions, to provide the frame 12, releasing the paddle 13 from the frame 12 by removing the clearance gap portion of the buried oxide layer; and forming a chemically sensitive coating 16 on a surface of the paddle 13.

Figure 5A:
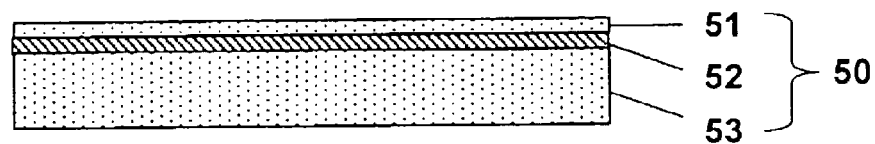
FIGS. 5a–5i illustrate a method to fabricate the teeter-totter resonator using micromachining techniques, starting with a silicon-on-insulator substrate.

In FIG. 5a is shown a cross section of a commercially available SOI substrate 50 comprising a top silicon layer 51 (e.g., 1- to 10-μm thickness) separated from a silicon substrate 53 (e.g., 400- to 500-μm thickness) by a buried oxide layer 52 (e.g., about 1 μm thickness). The SOI substrate 50 can be formed, for example, by a wafer bonding and etch-back method wherein a silicon wafer is thermally bonded to another silicon wafer by a thermally grown silicon dioxide intermediate layer. One of the silicon wafers is subsequently polished or etched down to the desired thickness to provide the top silicon layer 51. The top silicon layer 51 can therefore be single crystal silicon having good, consistent mechanical properties. The top silicon layer 51 can be undoped or lightly doped to provide low electrical conductivity. Alternatively, the top silicon layer 51 can be coated with a thin insulating layer (e.g., less than 50 nm of silicon nitride or silicon dioxide, not shown) to provide electrical isolation of the current conductor line 15. The buried oxide 52 provides a highly selective etch stop layer for subsequent etching of the top silicon layer 51 and the silicon substrate 53.

Figure 5B:
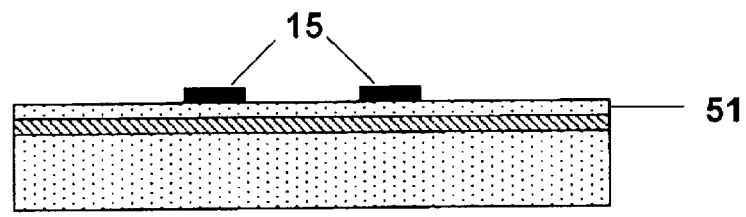

In FIG. 5b, a frontside metallization layer can be deposited and patterned on the top silicon layer 51 to provide the current conductor line 15. The frontside metallization layer can be patterned by a liftoff or an etch process, depending on the metal used. The metallization can comprise a high-conductivity metal, such as gold, aluminum, or platinum, having sufficient cross section to provide a current conductor line 15 having high electrical conductivity. The metal should also be compatible with subsequent processing. For example, the current conductor line 15 can be a gold line having a width of 40 μm and a thickness of 0.75 μm that can run around the periphery of the paddle 13.

Figure 5C:
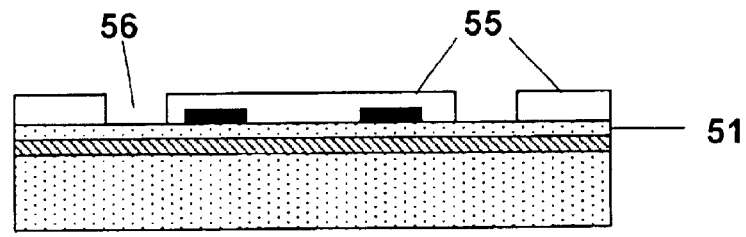

In FIG. 5c, a frontside photoresist layer 55 can be spun-on the front surface of the top silicon layer 51. The frontside photoresist layer 55 can be lithographically exposed and developed to provide openings 56 to define the paddle 13 and pivot arms 14 and the inner wall of the frame 12.

Figure 5D:
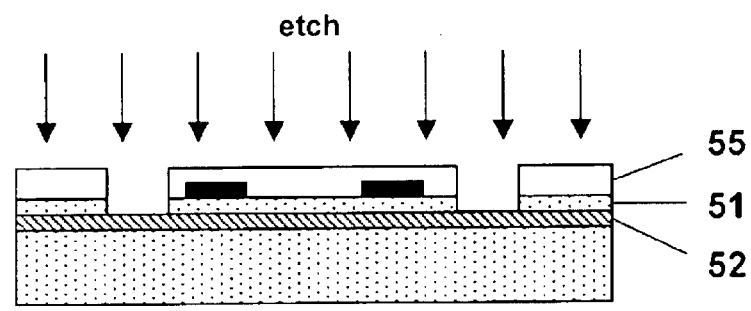

In FIG. 5d, the top silicon layer 51 can be patterned by etching through the openings 56 in the developed frontside photoresist layer 55 to provide the silicon portion of the paddle 13 and pivot arms 14. The exposed silicon can be removed by deep reactive ion etching (DRIE) using fluorine-based etchants (e.g., $SF_6$, $C_4F_8$). The DRIE etch will stop at the highly selective buried oxide layer 52 and provide well-defined, steep sidewalls in the patterned top silicon layer 51.

Figure 5E:
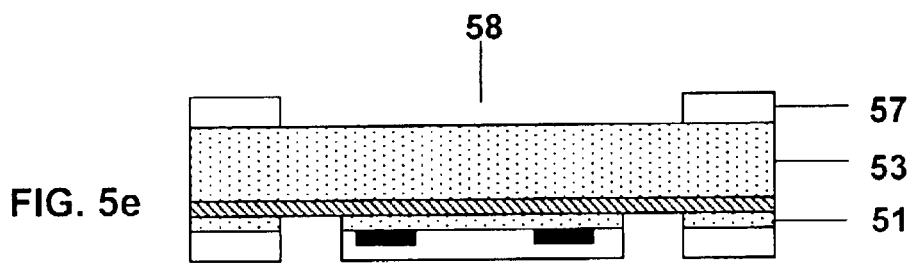

In FIG. 5e, the SOI substrate 50 can be flipped over and a backside photoresist layer 57 can be applied to the back surface of the silicon substrate 53. The photoresist layer 57 can be lithographically exposed and developed to provide an opening 58 to subsequently form a cavity in the silicon substrate 53 underneath the portion of the top silicon layer 51 that forms the paddle 13, pivot arms 14, and clearance gap 17.

Figure 5F:
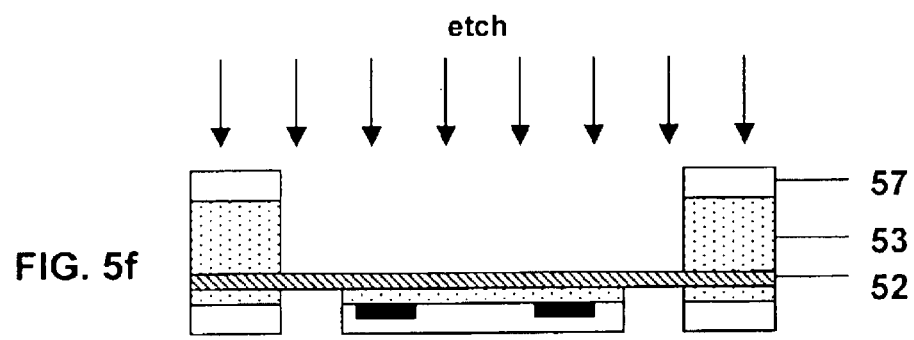

In FIG. 5f, the silicon substrate 53 can be etched through the opening 58 in the developed backside photoresist layer 57 by DRIE to form the cavity in the silicon substrate 53. The DRIE etch will effectively stop when it reaches the backside of the buried oxide 52.

Figure 5G:
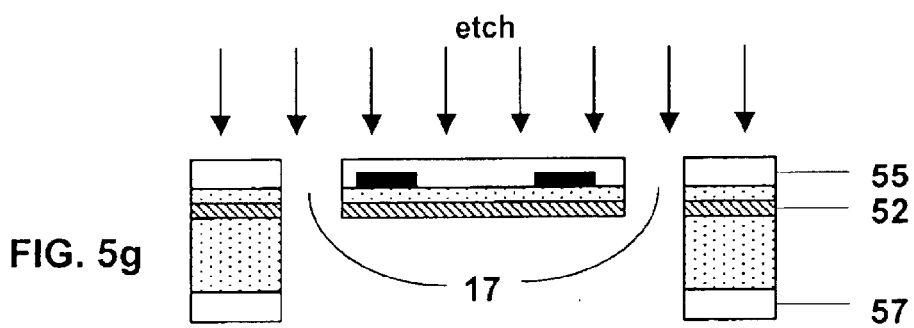

In FIG. 5g, the SOI substrate 50 can be flipped over and the frontside of the buried oxide layer 52 can be etched through the openings 56 in the developed frontside photoresist layer 55. The exposed silicon dioxide can be removed using a plasma-based etching process with fluorine-based etchants (e.g., $CHF_3$, $C_2F_6$) to complete the clearance gap 17 and release the structure. The clearance gap 17 allows the paddle 13 to freely oscillate within the cavity of the frame 12.

Figure 5H:
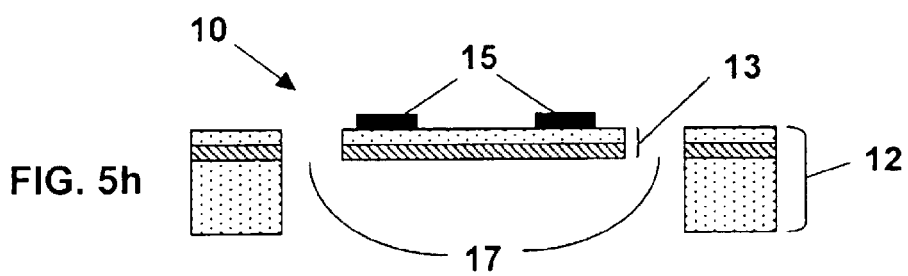

In FIG. 5h, the frontside and backside photoresist layers 55 and 57 can be stripped by standard solvents to provide the teeter-totter resonator 10, comprising the frame 12, paddle 13, pivot arms 14 (not shown in this cross-sectional view), and current conductor line 15.

Teeter-totter resonators can also be fabricated from other materials, such as polymers. For example, a teeter-totter resonator having a polyimide paddle can be fabricated from a stack comprising polyimide laminated between a copper layer and a stainless steel layer. The copper layer can be photopatterned and etched to form the current conductor line 15, and the stainless steel can be etched to form the paddle 13. The polyimide can then be laser trimmed to release the structure.

Figure 5I:
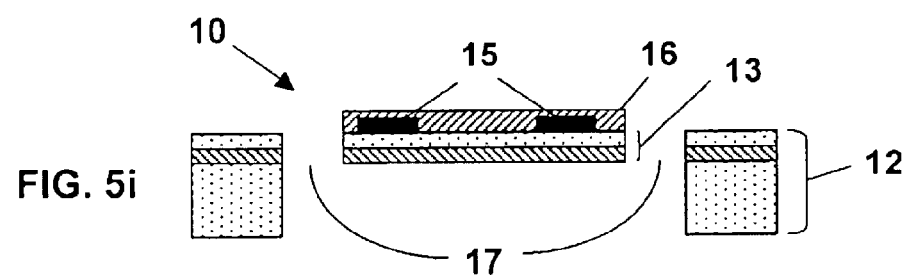

In FIG. 5i, a chemically sensitive coating 16 is preferably formed on one (as shown) or both surfaces of the paddle 13 to provide the microfabricated teeter-totter resonator 10 with enhanced ability to absorb chemical analytes from a fluid stream. The chemically sensitive coating 16 can be a chromatographic stationary phase, polymer, getter, or other sorbent material. Depending on the sorbent material, the coating can be applied by solvent casting, spraying, vapor deposition, electrochemical deposition, photo-polymerization, plasma polymerization, self-assembling deposition, photopatterning, or the like.

The coating 16 can be chosen to be sensitive to or have a high affinity for the analyte that one desires to detect. In addition, the coating 16 should preferably provide a rapid, reversible, and reproducible response to the sorbed analyte, stable chemical and physical properties, good adhesion to the paddle 13, and consistent coating behavior. Several types of polymer coatings, such as polyisobutylene, substituted polysiloxanes, and ethyl cellulose, have been developed for quartz crystal microbalances, SAW sensors, and FPW sensors. See J. W. Grate, "Acoustic Wave Microsensor Arrays for Vapor Sensing," *Chem. Rev.* 2000, 100, 2627–2648, which is incorporated herein by reference.

Mass can also be sorbed directly on the paddle material itself or by condensation or freezing of the analyte on the paddle 13. Consequently, analytes can be identified by their dewpoint or freezing temperature. Melting or evaporation of the collected analyte can be induced by heating the paddle 13 with increased current through the conductor line 15. In addition, fluid loading on the paddle 13 can also be used to differentiate gaseous or liquid species. The density and viscosity of the fluid will influence the damping coefficient of the resonator 10. Changes in the damping coefficient effect the magnitude and phase of the impedance, according to eqs. (9) and (10).

To improve detectability in a fluid stream containing multiple analytes, an array of resonators 10, each having a different partially selective coating 16, can be used. The response of each resonator 10 is thereby related to the different interactions between the analytes and the selective coatings 16. Therefore, such a sensor array ("electronic nose") can provide sensitivity over a wider range of analytes, improved selectivity, and simultaneous multicomponent analysis. In particular, the sensor array may be able to recognize individual analytes in a mixture, if a sufficiently diverse set of selective coatings 16 is used. Alternatively, an analytical instrument can comprise a gas chromatographic column or other separation means to separate the chemical analytes upstream of the resonator 10 and enable identification based on the time-of-arrival of the separated analytes at the resonator 10. In addition, for portable applications, the area occupied by the microfabricated resonators 10 can be relatively small and they can be integrated with on-board electronics to reduce the size and cost of the analytical instrument.

The method for chemical sensing of the present invention comprises providing the microfabricated teeter-totter resonator 10, applying the static magnetic field, energizing the current conductor line 15 with an alternating electrical current, exposing the resonator 10 to a chemical analyte in a fluid stream, and detecting the response of the oscillatory motion of the paddle 13 to the chemical analyte. Preferably, a chemically sensitive coating 16 is disposed on at least one surface of the paddle 13 to enhance sorption of the analyte. The mass change due to the sorbed analyte can be detected gravimetrically as a proportional change in the resonator's response. The response is generally electrically manifested as a change in the impedance of the current conductor line 15 due to a back-emf. The measured response can be a change in the resonant frequency $\omega_n$. The resonant frequency is inversely related to the moment of inertia of the paddle 13 and the combined mass of the paddle 13, coating 16, and sorbed or collected analyte. Alternatively, the sorbed analyte can be detected as a change in phase of the rotational displacement or drive voltage relative to the drive current. Therefore, the concentration of the analyte in a fluid stream can be determined by measuring the change in the resonant frequency $\omega_n$ or phase $\phi_d$ of the teeter-totter resonator 10 as a chemical analyte is absorbed on or desorbed from (i.e., added to or removed from) the paddle 13.

Figures 6A, 6B:
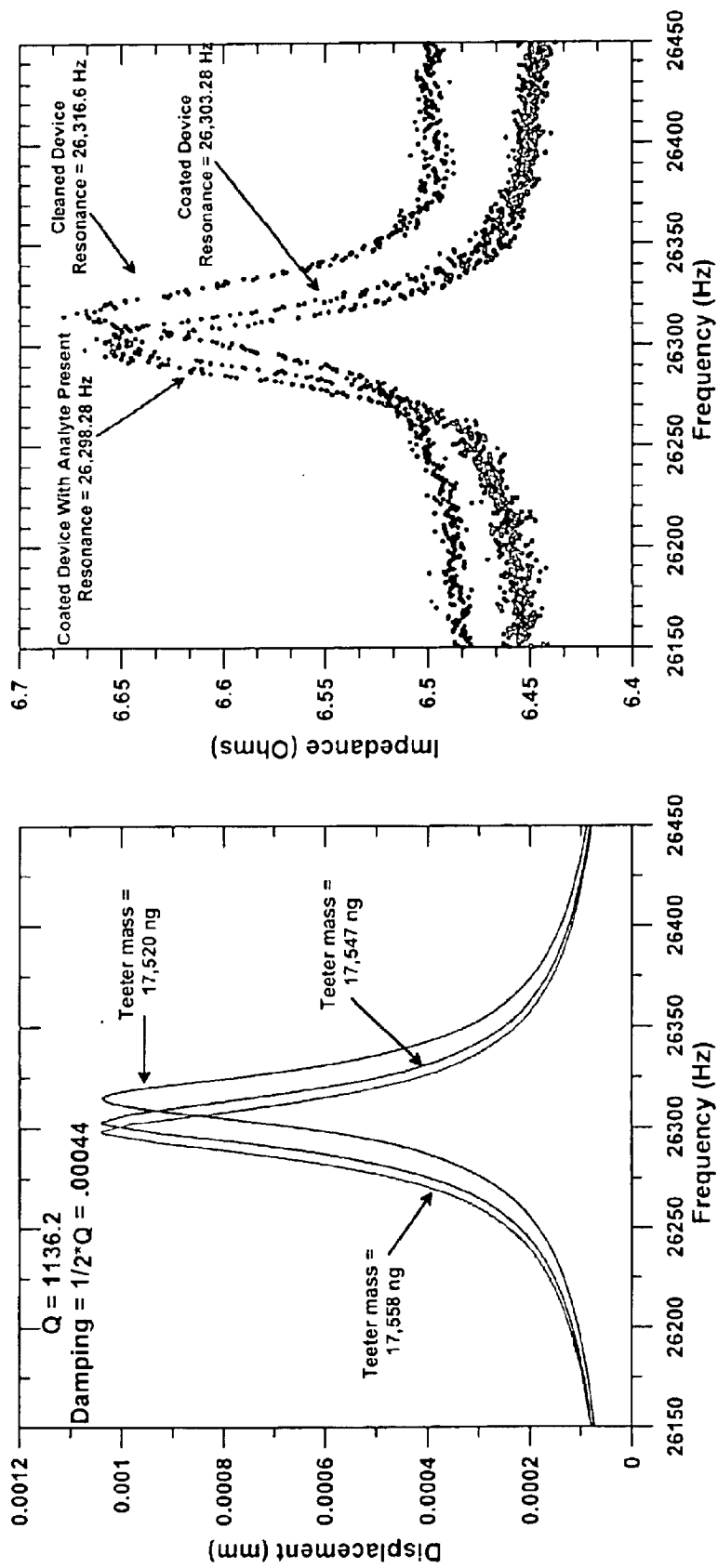
FIGS. 6a and 6b show the predicted paddle rotational displacement and the measured impedance as a function of frequency for microfabricated teeter-totter resonators having different paddle masses.

A finite-element model was used simulate the frequency response of a teeter-totter resonator when used as a chemical sensor. In FIG. 6a are shown the results of calculations of the paddle rotational displacement as a function of frequency for a teeter-totter resonator operated in air. The model assumed a silicon paddle that had a length of L=1.5-mm, width of w=0.6-mm and thickness of c=10-$\mu$m. The paddle mass was about 17.52 $\mu$g. The silicon pivot arms had a length of a=0.20-mm and a width of b=0.158-mm. The paddle and pivot arms material was silicon having an effective density $\rho$=2.91 g/cm$^3$ (i.e., including the gold electrode) and a shear modulus of G=64.5 Gpa. The applied magnetic field flux was B=0.18 Tesla. The calculations indicated a low operating frequency with a resonance for the bare paddle at about 26,317 Hz. The mass of the paddle was varied in the calculations to determine the sensitivity of the resonator to mass change. The resonant frequency is inversely related to the paddle mass, in agreement with eq. (6). The Q-factor was about Q ~1136.

In FIG. 6b is shown the measured impedance response for a cleaned (i.e., bare paddle) teeter-totter resonator, a coated resonator having a hydrogen-bond acidic polymer applied to the paddle, and the coated resonator with dimethylmethylphosphonate (DMMP) analyte present in the environment surrounding the resonator. The coating added about 27 ng and the analyte collected by the coating added about 11 ng to the mass of the paddle. The mass sensitivity of the frequency for this coated resonator was about 208 Hz/$\mu$g. Greater mass sensitivity, and lower levels of analyte detection, can be achieved by reducing the thickness, and therefore the mass, of the paddle.

An alternative approach to determining the resonant frequency $\omega_n$ is to track the phase difference between the drive voltage and drive current. If the resonator 10 is operated at a constant frequency near resonance by a frequency-controlled circuit, then minor changes in mass on the paddle 13 will cause a shift in the phase difference between the drive voltage and the drive current, as indicated by eq. (10).

Figures 7A, 7B:
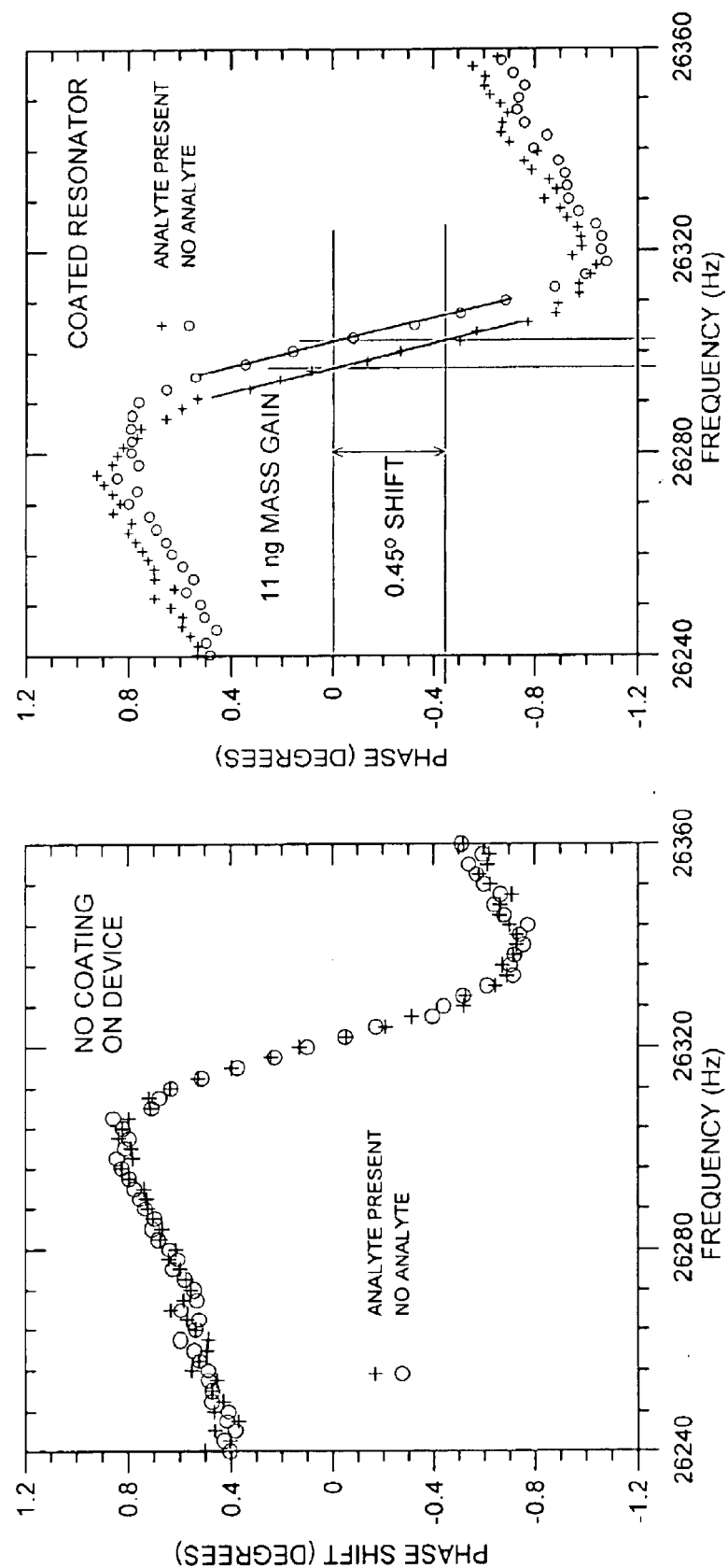
FIGS. 7a and 7b show the phase response as a function of frequency of an uncoated and a coated teeter-totter resonator before and after analyte is added to the environment surrounding the resonator.

A steep change in phase at resonance aids in the detection of nanogram levels of analytes. FIGS. 7a and 7b show phase change measurements that were made with a teeter-totter resonator, first tested without a coating (FIG. 7a) and then tested with a polymer coating (FIG. 7b). As shown in FIG. 7a, when there was no sorptive coating on the paddle, the zero phase crossing did not shift when DMMP was introduced into the environment surrounding the resonator. The lack of a phase shift indicates negligible absorption of analyte onto the native paddle surface. The mass sensitivity can be enhanced by using a chemically sensitive coating to increase the surface mass accumulation of the chemical analyte. As shown in FIG. 7b, the zero-phase crossing shifted by about 0.45° when analyte was introduced into the environment of the coated resonator. The mass sensitivity of the phase shift was about 0.04 degrees/ng for this coated resonator. Again, reducing the paddle thickness (i.e., mass) would increase the phase shift at resonance.

Figure 8:
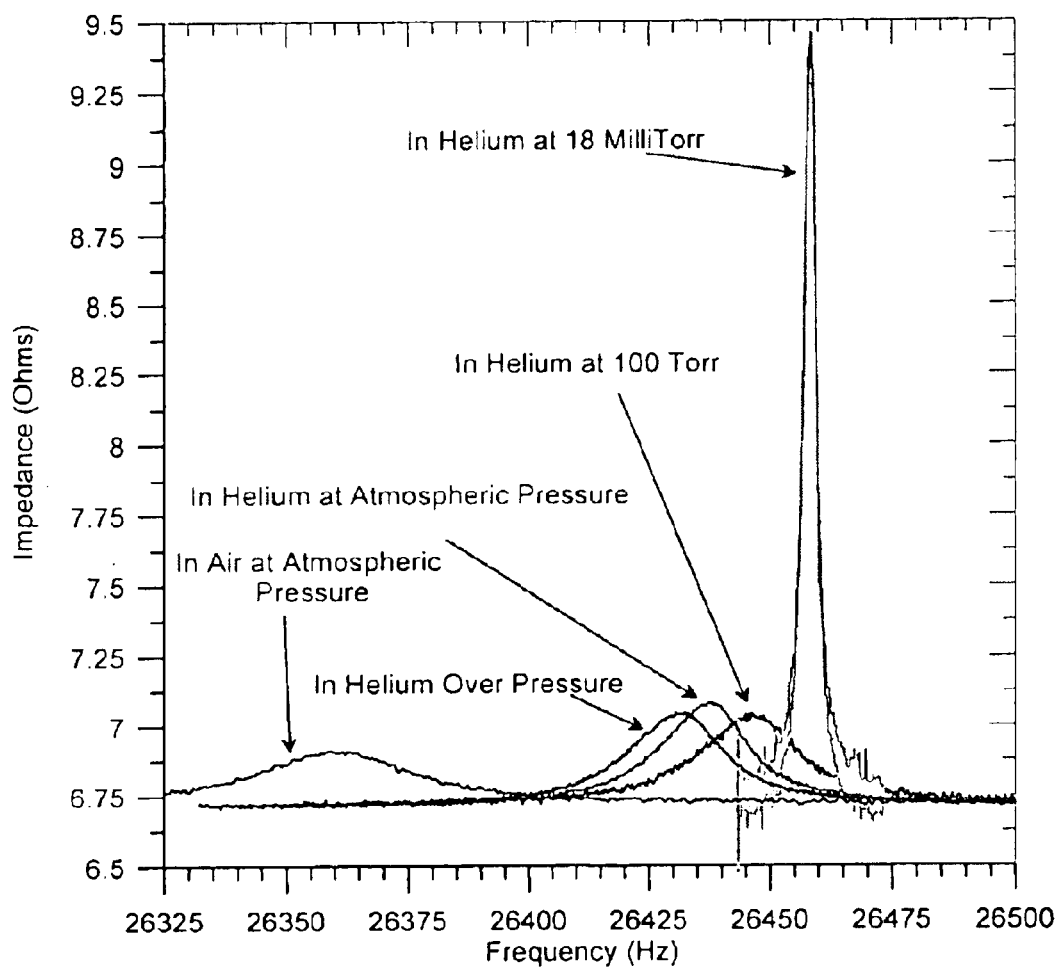
FIG. 8 shows the impedance response of a microfabricated teeter-totter resonator to fluid loading of various gas densities.

The teeter-totter resonator can also detect analytes by measuring the fluid loading of a fluid stream comprising the analyte. In FIG. 8 is shown the variation of resonant frequency as a function of fluid loading. Density variations in the surrounding gas alter the resonant frequency and quality factor of the resonator. The resonant frequency decreases as the ambient pressure increases (i.e., the gas loading increases). Additionally, the Q-factor increases (i.e., the width of the resonant peak increases) due to the increase in viscous dissipation at higher gas pressures. Furthermore, the resonant frequency is higher for lower molecular weight gases (i.e., helium) compared to higher molecular weight gases (i.e., air) at the same gas pressure. Therefore, the teeter-totter resonator can be used to identify gases and liquids by density and viscosity.

The present invention has been described as a method for chemical sensing using a microfabricated teeter-totter resonator. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for sensing a chemical analyte in a fluid stream, comprising:
   providing a microfabricated teeter-totter resonator, the resonator comprising:
      a frame,
      a paddle having a first end and a second end and wherein the paddle is pivotably anchored to the frame by pivot arms at each end of the paddle, the pivot arms defining an axis of rotation of the paddle,
      a current conductor line on a surface of the paddle that is displaced from the axis of rotation of the paddle,
      means for applying a static magnetic field aligned substantially in-plane with the paddle and substantially perpendicular to the current conductor line and the axis of rotation, and
      means for energizing the current conductor line with an alternating electrical current; and
   applying the static magnetic field;
   energizing the current conductor line with the alternating electrical current to excite an oscillatory motion of the paddle about the axis of rotation;
   exposing the resonator to the chemical analyte in the fluid stream; and detecting the response of the oscillatory motion of the paddle to the chemical analyte.

2. The method of claim 1, wherein the resonator further comprises a chemically sensitive coating disposed on at least one surface of the paddle for sorbing the chemical analyte from the fluid stream.

3. The method of claim 2, wherein the chemically sensitive coating comprises a polymer or getter.

4. The method of claim 1, further comprising collecting the chemical analyte on the paddle.

5. The method of claim 1, wherein the detecting comprises measuring the impedance of the current conductor line.

6. The method of claim 1, wherein the detecting comprises measuring the rotational displacement of the oscillatory motion of the paddle.

7. The method of claim 1, wherein the detecting comprises measuring the phase of the current relative to the voltage of the current conductor line.

8. The method of claim 1, wherein the detecting comprises measuring the phase of the current relative to the rotational displacement of the oscillatory motion.

9. The method of claim 1, wherein the resonator further comprises a second current conductor line on a surface of the paddle that is displaced from the axis of rotation of the paddle for detecting the oscillatory motion excited by the energizing of the current conductor line with the alternating electrical current.

10. The method of claim 9, wherein the detecting comprises measuring the output voltage induced in the second current conductor line.

11. The method of claim 1, wherein the current conductor line substantially follows the periphery of the paddle.

12. The method of claim 1, wherein the paddle comprises a rectangular shape.

13. The method of claim 1, wherein the frame comprises silicon.

14. The method of claim 1, wherein the paddle comprises silicon, polysilicon, silicon nitride, silicon dioxide, or a polymer.

15. The method of claim 1, wherein the energizing of the current conductor line with the alternating electrical current excites the oscillatory motion of the paddle in a resonant mode.

16. The method of claim 1, wherein the resonator further comprises a second paddle having a first end and a second end, and wherein the second paddle is pivotably anchored to the frame by pivot arms at each end of the second paddle, and wherein that the pivot arms of the second paddle are on the axis of rotation of the paddle and the current conductor line is further on a surface of the second paddle that is displaced from the axis of rotation to excite an oscillatory motion of the second paddle about the axis of rotation when the current conductor line is energized with the alternating electrical current.

17. The method of claim 16, wherein the current conductor line is disposed on the surface of the second paddle such that the oscillatory motion of the second paddle is counter-rotating to the oscillatory motion of the paddle.

18. The method of claim 16, wherein the current conductor line of the paddle and the second paddle is configured in a bridge circuit.

19. The method of claim 16, wherein a chemically sensitive coating is disposed on at least one surface of the second paddle for sorbing the chemical analyte from the fluid stream.

20. The method of claim 19, wherein the chemically sensitive coating comprises a polymer or getter.

* * * * *